United States Patent [19]

Biewenga et al.

[11] Patent Number: 5,925,668
[45] Date of Patent: Jul. 20, 1999

[54] THIOCTIC METABOLITES AND METHODS OF USE THEREOF

[75] Inventors: Gerreke Biewenga, Lund, Sweden; Guido R. M. M. Haenen; Aalt Bast, both of Amsterdam, Netherlands

[73] Assignee: ASTA Medica Aktiengesellschaft, Dresden, Germany

[21] Appl. No.: 09/009,770

[22] Filed: Jan. 20, 1998

Related U.S. Application Data

[60] Provisional application No. 60/037,648, Jan. 22, 1997.
[51] Int. Cl.$^6$ .................. A61K 31/385; A61K 31/22; A61K 31/185; C07D 339/02
[52] U.S. Cl. .................. 514/440; 514/550; 514/578; 549/39; 560/147; 562/512
[58] Field of Search .................. 514/440, 550, 514/578; 549/39; 560/147; 562/512

[56] References Cited

U.S. PATENT DOCUMENTS

| | | | |
|---|---|---|---|
| 4,966,732 | 10/1990 | Giray et al. | 549/39 |
| 5,489,694 | 2/1996 | Paust et al. | 549/39 |

OTHER PUBLICATIONS

Teichert, J., et al. "Determination of lipoic acid in human plasma by high–performance liquid chromatography with electrochemical detection", Journal of Chromatography B: Biomedical Applications, vol. 2, No. 672, Oct. 20, 1995, pp. 277–281.

*Primary Examiner*—Deborah C. Lambkin
*Attorney, Agent, or Firm*—Pillsbury Madison & Sutro LLP

[57] ABSTRACT

The present invention provides compounds with antioxidant activity effective in treating free radical mediated diseases.

6 Claims, 6 Drawing Sheets

FIG. 4A lipoic acid methylester

FIG. 4B 3-ketolipoic acid methylester

THIOCTIC METABOLITES AND METHODS OF USE THEREOF

This is a Continuation-in-Part of National Appln. Ser. No. 60/037,648 filed Jan. 22, 1997.

BACKGROUND OF THE INVENTION

Lipoic acid (1,2-dithiolane-3-pentanoic acid) is a naturally occurring compound. It is a component of mitochondrial multienzyme complexes which dehydrogenates a-keto acids (e.g. pyruvate). In pathological conditions, lipoic acid is applied in the treatment of diabetic polyneuropathy, liver cirrhosis and metal intoxications. Particularly in diabetic polyneuropathy, the antioxidant activity of lipoic acid is considered to contribute to its therapeutic effect.

The metabolism of lipoic acid has been studied in *Pseudomonas* (Furr et al., *Arch. Biochem. Biophys.* 185:576–583 (1978)) and in rats (Spence et al., *Arch. Biochem. Biophys.* 174:13–19 (1976); Gal et al., *Arch. Biochem. Biophys.* 89:253–261 (1960); Harrison et al., *Arch. Biochem. Biophys.* 160:514–522 (1974)). It has been found that in these species lipoic acid is converted by beta oxidation of its pentanoic acid side chain. Regarding the antioxidant activity of lipoic acid, it has been speculated that reduction of lipoic acid to dihydrolipoic acid is an important step in its therapeutic effect. However, no data on the metabolism of lipoic acid in humans is available. Since insight in the kinetics and metabolism of lipoic acid is needed for fully apprehending the pharmacotherapeutic effect, we studied the absorption, metabolism and excretion of lipoic acid.

The lack of knowledge on the pharmacokinetics of lipoic acid is due to the laborious and/or non-specific analytical methods which were available for its detection in biological samples. In the 1960–1970's, only thin layer chromatographic, microbiological and gas chromatographic methods were available. In 1981, HPLC was first applied to the analysis of lipoic acid (Howard et al., *J. Chromatogr.* 208:129–131 (1981)). This method was suitable for the separation of lipoic acid and several structurally related compounds. However, the UV detection at 330 nm that was applied resulted in a high limit of detection. Later, electrochemical detection (ECD) was used, thus greatly improving the sensitivity of detection in HPLC (Teichert et al., *Naunyn-Schmiedeberg's Arch. Pharmacol., Suppl* 344:R91 (1991); Kamata et al., *J. Pharmaceut. Biomed. Anal.* 8:453–456 (1990); Teichert et al., *J. Chromatogr. B* 672:277–281 (1995)). In this paper we describe an HPLC/ECD method for the detection of lipoic acid and its metabolites in a single run. After oral administration of 1 gram R-lipoic acid to a human volunteer, the plasma concentration of lipoic acid and the metabolites were followed over a 5 hour period. In addition, we elucidated the structure of an unknown metabolite. The pharmacokinetic profile of lipoic acid is discussed in view of its antioxidant activity and its therapeutic application.

SUMMARY OF THE INVENTION

The present invention provides a method of treating free radical mediated diseases, and/or reducing the symptoms associated with such diseases, comprising administering an effective amount of a compound of the formula wherein $R_1$ and $R_2$ are independently (=O) or —OR, where R is H or ($C_1$–$C_4$) alkyl; and $R_3$ is H or ($C_1$–$C_4$) alkyl. Preferably, $R_3$ is H. Preferably $R_1$ and $R_2$ are (=O) or OH.

In a more preferred embodiment, the compound is of the formula wherein X is H or both Xs represent a direct bond between the two sulfur atoms; $R_1$ is (=O) or —OH; and $R_2$ is H, Na, K or ($C_1$–$C_4$)alkyl In a particularly preferred embodiment of the invention, the compound is 3-keto lipoic acid, 3-hydroxy lipoic acid, 3-keto dihydrolipoic acid or 3-hydroxy dihydrolipoic acid.

Free radical mediated diseases include diabetic polyneuropathy, liver cirrhosis and metal intoxication.

DETAILED DESCRIPTION OF THE INVENTION

After oral administration of one gram R-lipoic acid to a human volunteer, lipoic acid, 3-ketolipoic acid and bisnorlipoic acid were detected in the plasma by means of HPLC coupled to electrochemical detection. The maximum concentration of lipoic acid (1154 ng/ml), 3-ketolipoic acid (2092 ng/ml), and bisnorlipoic acid (704 ng/ml) were observed at 92 min, 119 min, and 189 min respectively. The detection of these compounds and their sequential formation in time suggests that lipoic acid is extensively metabolized via beta-oxidation. Lipoic acid levels declined relatively fast (half life ca. 1 hr). The metabolite 3-ketolipoic acid was found in higher concentration than lipoic acid and these plasma levels maintained for a longer period than the lipoic acid level. 3-Ketolipoic acid contains the 1,2-dithiolane ring which is held responsible for antioxidant activity. Based on its plasma levels and based on its molecular structure, we suggest that the metabolite 3-ketolipoic acid is a major contributor to the antioxidant activity of lipoic acid in vivo. The therapeutic effectiveness of lipoic acid in free radical mediated diseases may originate to some degree from 3-ketolipoic acid.

To fully understand the pharmacotherapeutic effect of lipoic acid insight into the kinetics and metabolism of lipoic acid is necessary. For a long time the existing analytical methods were not sensitive and selective enough to determine the pharmacokinetics of lipoic acid. However, over the past 15 years HPLC techniques to analyze lipoic acid have improved. Howard and McCormick (Howard et al., *J. Chromatogr.* 208:129–131 (1981)) applied the HPLC technique for the first time for relatively pure mixtures of lipoic acid and several analogues. Kamata and Akiyama (*J. Pharmaceut. Biomed. Anal.* 8:453–456 (1990)) further developed the method for quantification of lipoic acid in tablets. Recently, Teichtert and Preib (*J. Chromatogr. B* 672:277–281 (1995)) described a HPLC analysis of lipoic acid levels in human plasma. The applied HPLC/ECD technique in our study is suitable to detect tetranorlipoic acid, bisnorlipoic acid, lipoic acid and dihydrolipoic acid simultaneously. In human plasma bisnorlipoic acid and lipoic acid are well separated from the other plasma components (nrs 4 and 7 in FIG. 2). In addition, it was possible to detect two unknown metabolites of lipoic acid in the plasma with the applied method (nrs 5 and 6 in FIG. 2). The detection of dihydrolipoic acid in plasma is possible but hampered by its is rapid oxidation by plasma components.

Figure 2A:
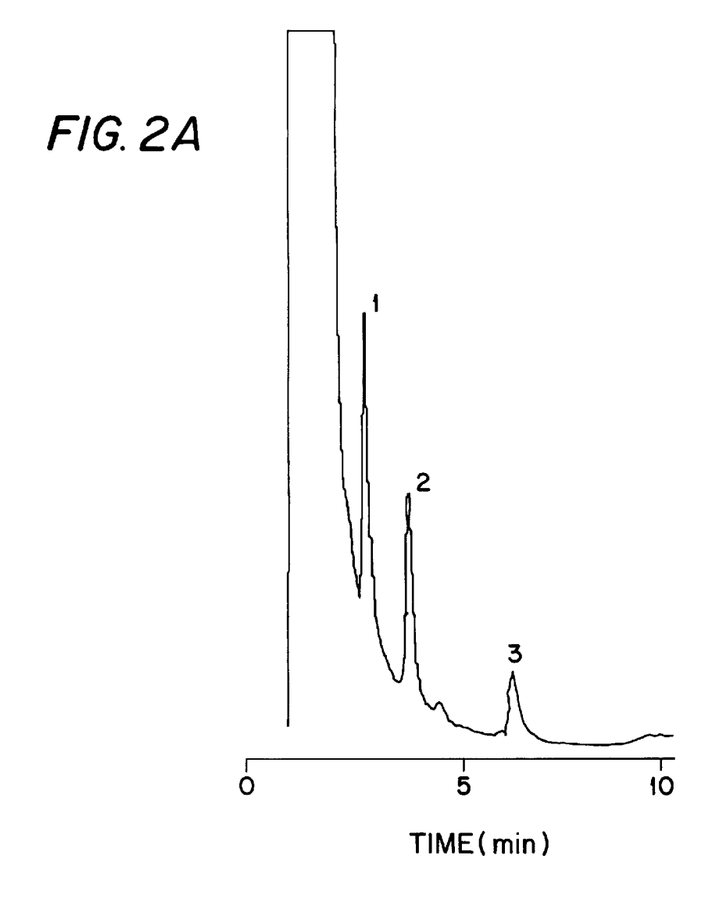
FIG. 2. The HPLC chromatogram of the plasma sample before oral administration of lipoic acid (panel A) and the HPLC chromatograph of the plasma sample 119 min after oral administration of 1 gram R-lipoic acid to a healthy, male volunteer (panel B). The peaks numbered 1, 2 and 3 were from endogenous compounds in the plasma. Peak number 4 was identified as bisnorlipoic acid, number 5 is an unidentified metabolite of lipoic acid, number 6 was identified by GC/MS as 3-ketolipoic acid, and peak number 7 is lipoic acid.
Figure 2B:
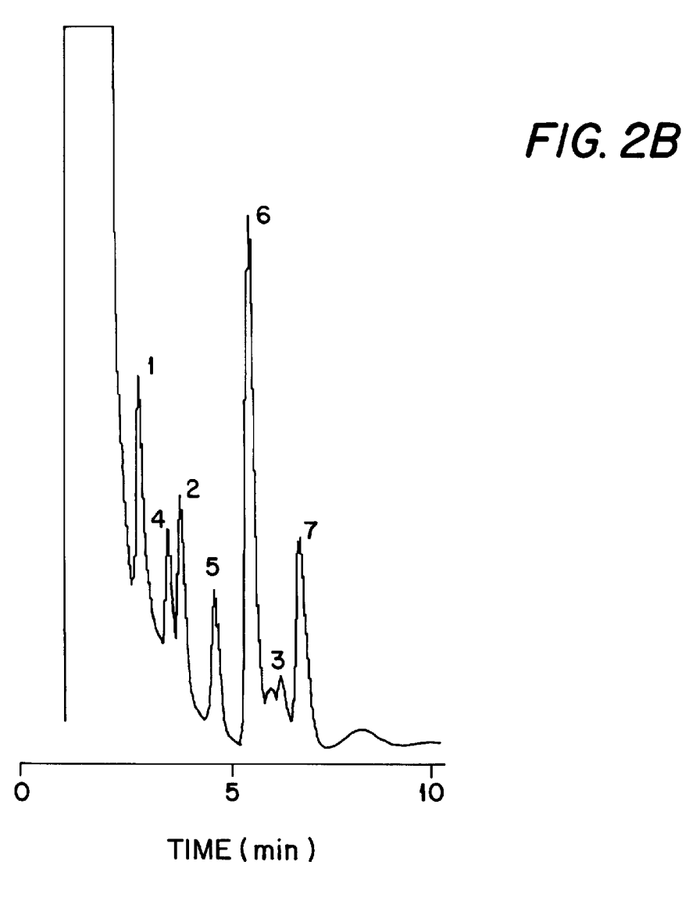

Both the method of Teichert and Preib (*J. Chromatogr. B* 672:277–281 (1995)) and our method are suited for the detection of lipoic acid in human plasma. The most prominent difference between the methods is that we omitted a hydrolysis step in the clean-up procedure. Consequently, the analysis we described is useful to determine the plasma concentrations of free compounds. Under normal physiological conditions, lipoic acid is covalently bound to a lysine residue of the multienzyme complexes. Indeed, we did not detect free lipoic acid before administration of lipoic acid (FIG. 2A). This indicates that free lipoic acid concentrations in plasma are low (<7.8 ng/ml). By introducing a hydrolysis step this, bound lipoic acid is detected, as was observed by Teichert and Preib (*J. Chromatogr. B* 672:277–281 (1995)). However, lipoic acid is administered therapeutically in relatively high doses compared to dietary intake. Consequently, after administration of lipoic acid in therapeutic doses free lipoic acid will become available. Indeed, we detected free lipoic acid after administration of lipoic acid (FIG. 2B). Based on studies of the molecular mechanism of lipoic acid it is suggested that the therapeutic effect of lipoic acid is probably due to the free compound which acts as an antioxidant. This implies that the therapeutic effect is related to the concentrations of the free lipoic acid, which is measured by our method.

Figure 3:
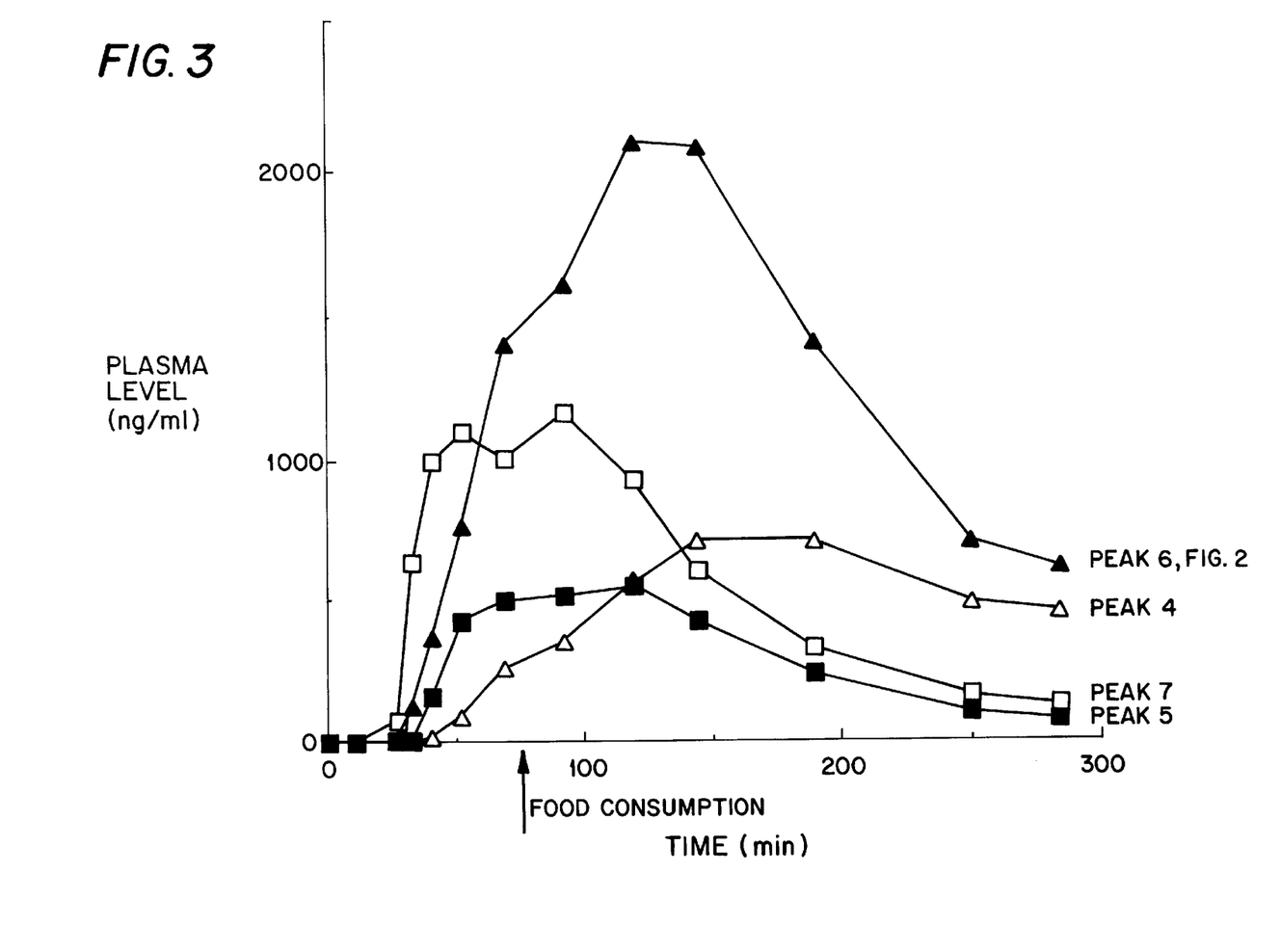
FIG. 3. The time course of the plasma concentration of lipoic acid, n a metabolite which eluted in peak 5 of FIG. 2 (probably 3-hydroxylipoic acid), D a metabolite which eluted in peak 6 of FIG. 2 (identified as 3-ketolipoic acid), and D bisnorlipoic acid after oral administration of 1 gram R-lipoic acid to a healthy volunteer who fasted overnight. A meal high in fat content was consumed 85 minutes after the oral intake of R-lipoic acid. The concentrations of the metabolites were calculated on the calibration curve of lipoic acid.

FIG. 3 shows the time course of the plasma concentration of lipoic acid during a time period of 5 hours after oral administration of 1 gram R-lipoic acid. Lipoic acid appears in the blood plasma after 30 min. The elimination of lipoic acid showed first order kinetics with a half life of 56 min. A diet with a high fat content was consumed after 85 min, which coincided with a second increase in plasma level. This indicates that absorption of lipoic acid is stimulated by food consumption and possibly by fatty intake. Apparently, the diet of a patient will influence the plasma level and thereby the therapeutic efficiency of orally administered lipoic acid. The observed maximal plasma concentration of lipoic acid is 1154 ng/ml (FIG. 3). For comparison, Teichert and Preib (cited above) observed after oral application of only 200 mg R/S-lipoic acid in two healthy volunteers, obtained under controlled conditions, a maximal plasma level of ca. 400 ng/ml and ca. 1200 ng/ml. The concentration-time profiles of the two volunteers reported by Teichert and Preib varied from one another. This indicates that there is a high inter-individual variation in the absorption of lipoic acid. Both the influence of the diet and the inter-individual variation in absorption will induce large differences in patient groups in clinical trials where lipoic acid is given orally. This might explain why the therapeutic effect of lipoic acid after oral dosage in clinical studies is more difficult to detect than the therapeutic effect after intravenous administration (Ziegler et al., *Diabetologia* 38:1425–1433 (1995)).

It is widely believed that the therapeutic action of lipoic acid is based on its antioxidant activity (Packer et al., *Free Rad. Biol. Med.* 19:227–250 (1995)). The metabolites of lipoic acid may also be involved in its therapeutic effect. It has been speculated that reduction of lipoic acid into dihydrolipoic acid is one of the key processes in the antioxidant activity of lipoic acid. The reduction of lipoic acid was shown in human cells in culture (Handelman et al., *Biochem. Pharmacol.* 47:1725–1730 (1994)) and in human erythrocytes (Constantinuseu et al., *Biochem. Pharmacol.* 50:253–261 (1995)). Our assay, and particularly the sample pretreatment, was designed to detect potentially formed dihydrolipoic acid. Nevertheless, no dihydrolipoic acid was detected in human plasma after administration. An explanation for the absence of dihydrolipoic acid may be that reduction takes place only intracellularly (e.g., by lipoamide dehydrogenase). This reduction may not be reflected by a detectable dihydrolipoic acid concentration in plasma. A second explanation for the absence of dihydrolipoic acid may be found in the high reactivity of dihydrolipoic acid. In accordance with the observations of Teichert and Preib (cited above), we found that the stability of dihydrolipoic acid in plasma is poor. In aqueous solutions dihydrolipoic acid appeared to be more stable. This indicates that dihydrolipoic acid reduces plasma components more rapidly than that it is oxidized by air. In fact, reduction of plasma components as dehydroascorbic acid and GSSG results in regeneration of the antioxidants vitamin C and GSH. This is thought to be the major mechanism of antioxidant activity derived from dihydrolipoic acid. Therefore, the failure to detect dihydrolipoic acid in plasma is still in line with the hypothesis that the formation of dihydrolipoic acid is essential in the therapeutic effect of lipoic acid. It may indicate that the antioxidant reactivity is even larger than originally thought.

Figure 4A:
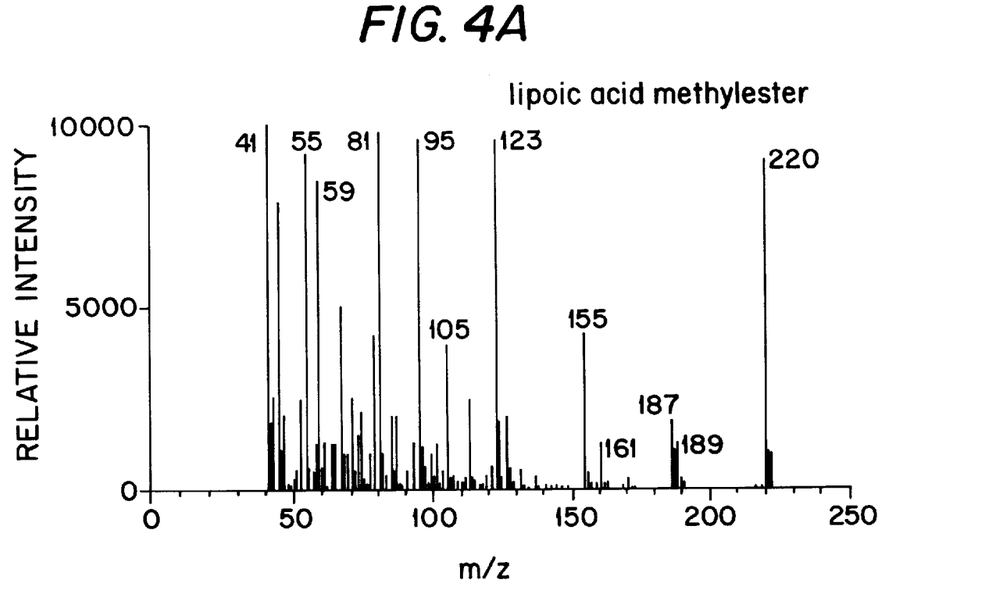
FIG. 4. Top: the mass spectrum obtained by electron impact ionization of the standard lipoic acid methyl ester which eluted at 10.46 min from the GC column. Bottom: the mass spectrum obtained by electron impact ionization of the unknown metabolite (peak number 6 in FIG. 2) which eluted at 12.20 min from the GC column and was identified as 3-ketolipoic acid.
Figure 4B:
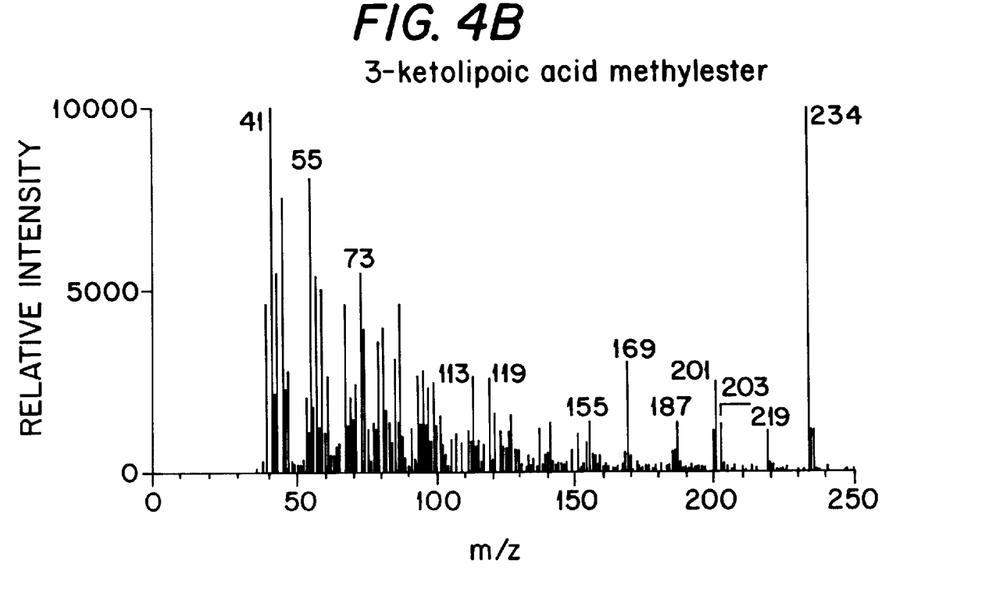
Figure 5:
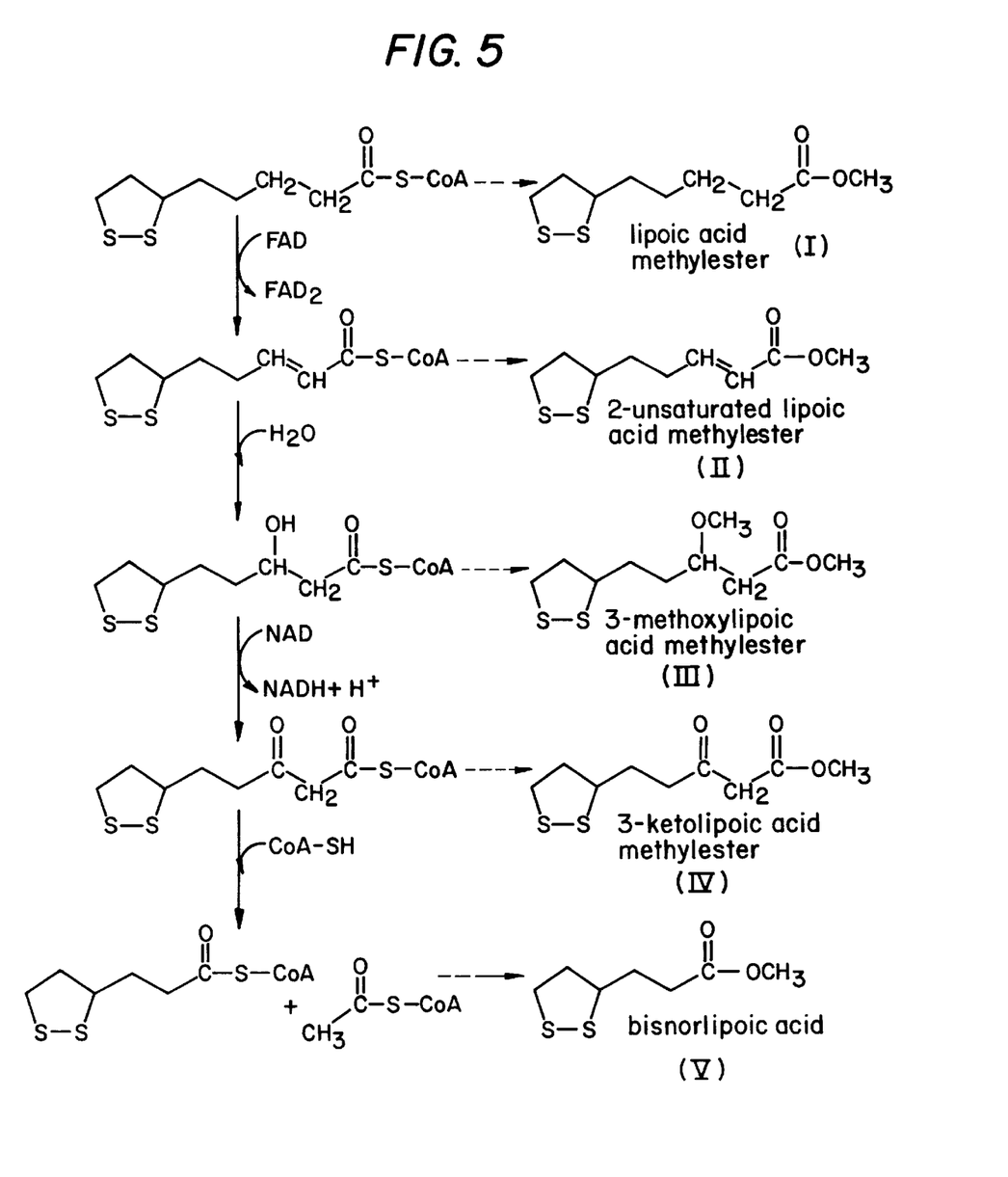
FIG. 5. The reaction sequence of the degradation of fatty acids (left-hand side). The GC/MS chromatogram of the pooled plasma sample from t=69, 92 and 119 min was searched for the compounds shown at the right-hand side. It was hypothesized that after release of HSCo-enzyme A the free acid is formed. For identification by GC/MS the compounds were methylated by diazomethane which resulted in the depicted methyl esters.

Evaluating the pharmacokinetic data, it is observed that over a period of several hours lipoic acid is metabolized extensively via beta oxidation. Bisnorlipoic acid (nr. 4 in FIG. 2) and two unknown metabolites (nrs. 5 and 6 in FIG. 2) appear in the chromatograph. The metabolite with peak number 6 was present in relatively high concentrations and could be identified as 3-ketolipoic acid. Teichert and Preib observed an unknown metabolite with a lower retention time than lipoic acid. This may be the same metabolite which we identified as 3-ketolipoic acid. These findings indicate that beta oxidation is a significant route of metabolism in humans, comparable to metabolism in Pseudomonas and rats. We tentatively identified a metabolite number 5 (FIG. 2) as 3-hydroxylipoic acid (of which the methylated structure is shown in FIG. 4). From the HPLC and GC profile it is concluded that the compound eluting in peak nr 5 is more hydrophilic and its methylester less volatile than 3-ketolipoic acid (peak 6 in FIG. 2) and lipoic acid. Secondly, in the time-profile of the plasma concentrations (FIG. 3) the compound derived from peak 5 reaches its maximal level before the compound from peak 6 reaches maximum. This suggests that the compound from peak 5 is formed earlier than the compound from peak 6. Indeed, 3-hydroxylipoic acid is formed before 3-ketolipoic acid in the beta oxidation sequence (FIG. 5). Unfortunately, the concentration of the compound is too low to confirm the proposed identity with GC/MS.

As already mentioned, the therapeutic effect of lipoic acid is linked to its antioxidant activity. Also, the beta oxidation products may contribute to the antioxidant effect and, thereby, to therapeutic activity. The 1,2-dithiolane ring structure is of importance in the antioxidant activity. This ring structure provides bisnorlipoic acid with its HOCl scavenging capability (Biewenga et al., *Arch. Biochem. Biophys.* 312:114–120 (1994)). Reduction of the 1,2-dithiolane into the dithiol of bisnorlipoic acid results in scavenging capability of superoxide and peroxyl radicals (Dikalov et al., *Arch. Biochem. Biophys.* 326:207–218 (1996); Suzuki et al., *Free Rad. Res. Comms.* 18:115–122 (1993)).

3-Ketolipoic acid also contains the 1,2-dithiolane ring structure. Therefore, it is expected that this compound also has considerable antioxidant activity. Additionally, the keto group next to the carboxyl group may provide extra metal chelating properties compared to lipoic acid which may be important for antioxidant activity. Assuming that the recovery and electrochemical response of 3-ketolipoic acid and lipoic acid are comparable, 3-ketolipoic acid is present in higher plasma concentrations for a longer period of time than lipoic acid. If the plasma concentrations reflect the concentration at the site of action and assuming a comparable therapeutic efficacy as lipoic acid, 3-ketolipoic acid will be the major contributor to the therapeutic effect of lipoic acid. This would be in line with the dose regime of lipoic acid. Lipoic acid is administered twice daily. After three hours, lipoic acid was essentially absent from the plasma (FIG. 3). For an efficient protection against oxidative stress a high concentration of scavenger has to be present constantly. In the time span between two administrations, after a rapid increase, the concentration of lipoic acid will fall to a concentration too low to afford effective protection. The concentration of 3-ketolipoic acid, however, remains high for a longer time period compared to lipoic acid.

3-ketolipoic acid may be a noteworthy metabolite of lipoic acid. 3-ketolipoic acid appears in relatively high concentrations in plasma and it has structural characteristics of an antioxidant. 3-ketolipoic acid may have even higher therapeutic activity than its parent compound, lipoic acid.

EXAMPLES

Materials and Methods

The following abbreviations are used herein: HPLC (high performance liquid chromatography); ECD (electrochemical detection); GC (gas chromatography); GSH (glutathione); GSSG (oxidized glutathione); i.d. (internal diameter); and MS (mass spectrometry).

Chemicals

R-lipoic acid, racemic dihydrolipoic acid, bisnorlipoic acid, tetranorlipoic acid and lipoic acid methyl ester were gifts of ASTA Pharma A.G. (Frankfurt am Main, Germany). Acetonitrile and methanol were of HPLC grade from Baker; Phosphoric acid was obtained from Merck. The chemicals used were of analytical grade purity.

Chromatography

The HPLC system consisted of a pump (thermo separation products, Spectra SERLES P100,Breda, the Netherlands), an auto-injector (Gilson, Meyvis, model 232 XL, Bergen op Zoom, the Netherlands) with a 20 ml sample loop and a dilutor (Gilson, Meyvis, model 401 C, Bergen op Zoom, the Netherlands). The system was equipped with an electrochemical detector (Coulochem ESA, model 5100 A, Interscience, Breda, the Netherlands) and an analytical cell (ESA, model 5010). Interscience, Breda, the Netherlands) which consisted of two cell compartments. The optimal potentials of both compartments have been determined (vide infra): cell 1 had a potential of 500 mV and cell 2 of 800 mV (unless otherwise noted).

The separations were performed using a Hypersil C 18 column (125 mm×4.6 mm i.d., 3 mm particle size) and a mobile phase of phosphate buffer (50 mM $KH_2PO_4/H_3PO_4$, pH 2.7) and acetonitrile (65:35, v/v). Before use, the eluent was vacuum filtrated over a 0.45 mM filter. The flow rate was 0.7 ml/min.

Sample Collection and Preparation

To a healthy volunteer (male, 35 years, 82 kg), who fasted overnight, 1 gram of R-lipoic acid (4 capsules of 250 mg) was administered orally. At several time points (0–5 hr), blood samples of 3 ml were taken from a venous cannula into Li-heparine containing tubes. The samples were centrifuged (2000 g at 4° C. for 5 min) and the plasma was analyzed immediately. The proteins in the plasma were precipitated by adding 1 ml ethanol and 7.5 ml 85% (g/g) $H_3PO_4$ to 500 ml plasma. Thereafter, the sample was thoroughly mixed on a vortex mixer and placed on ice. After 15 min it was centrifuged at 2000 g for 10 min at 4° C. Twenty ml of the supernatant were brought onto the column. Quality control samples were prepared by spiking plasma with a small volume (less than 1%) of an ethanol solution of the compound.

Determination of the Molecular Structure of the Unknown Metabolite

For the elucidation of the structure of the metabolites, the plasma obtained at 69, 92 and 119 min was pooled (approximate total volume was 3 ml). The pooled plasma was acidified with 3 ml 3 M sulfuric acid. Thereafter, the sample was extracted twice with 12 ml HPLC-grade ethylacetate (Baker Phillipsburg, N.J.). After evaporation of the ethylacetate the compounds were methylated with diazomethane for 30 min at room temperature. Subsequently, the compounds were dissolved in 50 ml ethanol. A volume of 0.8 ml was injected on a GC/MS system using a split injection ratio of 1/15. The instrument used was a HP 5890 GC equipped with a HP 5970 mass selective detector. Gas chromatography was performed on a CPSil 5 CB WCOT capillary column (25 m, 0.2.5 mm i.d., 0.2 mm thickness; Chrompack, Middelburg, the Netherlands). While the temperature of the injector and transfer line were kept at 250° C., two oven temperature programs were required to obtain satisfactory separation of all lipoic acid related components from endogenous plasma components. The oven temperature was programmed from 60° C. (kept for 2 min) to 180° C. (at 20° C./min) with an isothermal period (10 min) and subsequent temperature increase to 288° C. (at 20° C./min) and another isothermal period; this produced satisfactory results for all components except bisnorlipoic acid. Bisnorlipoic acid could be separated from background components by using a program from 60° C. (kept for 2 min) to 160° C. (at 20° C./min with an isothermal period (15 min) and subsequent raise to 288° C. (at 20° C./min). Detection was performed by using 70 eV impact ionization.

RESULTS

Detection

Figure 1A:
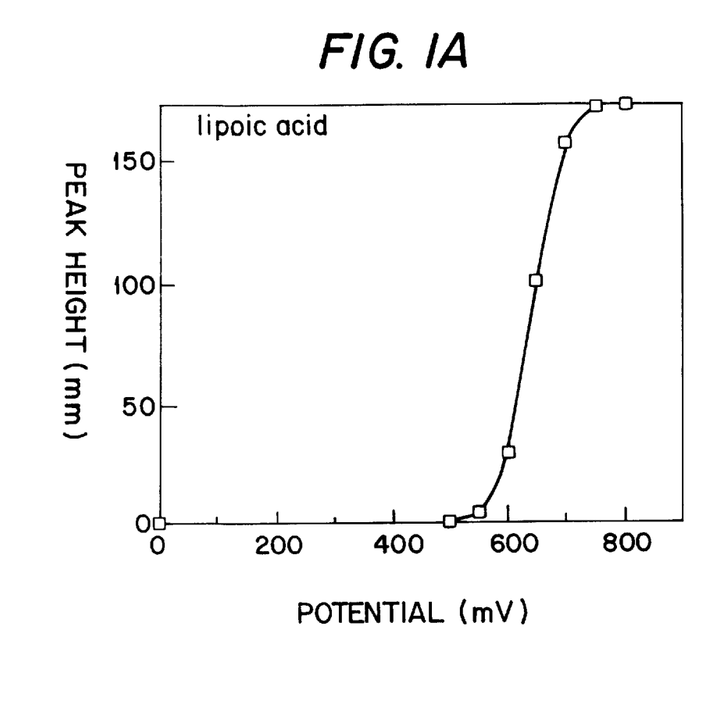
FIG. 1. The current-potential curve for lipoic acid (left) and dihydrolipoic acid (right) using a concentration of 10 mg/ml eluens (50 mM $KH_2PO_4$/$H_3PO_4$, pH 2.7) and acetonitrile (65:35, v/v)). The voltage of cell 1 of the electrochemical detector (Coulochem ESA) was held constant at 0 mV. The voltage of cell 2 was varied from 500 mV to 800 mV.
Figure 1B:
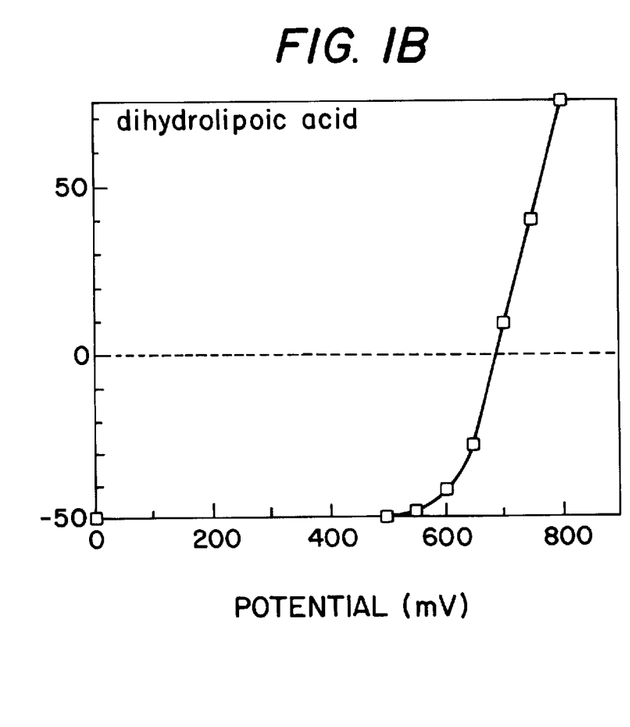

For detection of the compounds after HPLC separation, electrochemical detection was used. For lipoic acid the current-potential curve is shown in FIG. 1. Lipoic acid is not oxidized at 500 mV. At 800 mV a maximal current is obtained. Based on these results, cell 1 was adjusted to 500 mV and cell 2 to 800 mV. In this way, an optimal sensitivity with high selectivity is obtained because compounds in plasma which oxidize below 500 mV in cell 1 are not detected by the system while lipoic acid itself is not oxidized.

For dihydrolipoic acid the current-polential curve is also shown in FIG. 1. Dihydrolipoic acid shows a positive signal above 700 mV and a negative signal between 500 mV and 700 mV. The results indicate that at 800 mV lipoic acid and dihydrolipoic acid can be detected simultaneously. On a molar basis, lipoic acid produces a higher signal than dihydrolipoic acid at this potential.

Chromatography

A reversed phase system using a mixture of phosphate buffer (50 mM $KH_2PO_4/H_3PO_4$, pH 2.7) and acetonitrile (65:35, v/v) was applied. Lipoic acid is well separated from dihydrolipoic acid, bisnorlipoic acid and tetranorlipoic acid. The retention times are 7.1 min, 8.6 min, 3.6 min and 2.6 min, respectively.

A calibration curve was constructed using calibrators containing 0.05, 0.1, 0.2, 0.5, 1.0, 2.0 and 5.0 mg lipoic acid or dihydrolipoic acid per ml eluens. The calibrators were prepared by dissolving the analytes in methanol and diluting it to the appropriate concentration in eluent. The calibrators were directly injected.

A linear relation was found between the amount of dihydrolipoic acid or the amount of lipoic acid injected versus the peak height with a good correlation (R=0.993 and R=1.000 respectively).

The accuracy and precision were determined by analyzing quality control samples in four different analytical batches. The quality control samples were prepared by spiking plasma with dihydrolipoic acid or lipoic acid at two concentration (final concentration: 0.5 mg/ml and 5 mg/ml) just before deproteination of the plasma by adding ethanol and phosphorous acid. At both concentrations, the accuracy for dihydrolipoic acid and lipoic acid, calculated on the calibration line constructed in eluent, were 70% and 92% respectively. The overall precision of the dihydrolipoic acid and lipoic acid determination were 10% and 3% respectively.

The stability of lipoic acid in plasma was evaluated by spiking plasma at 0.5 mg/ml and storing it at -25° C. After approximately 20 hours, the concentration found was 96±1% of the theoretical value. After one week, the concentration found was 93% of the theoretical value. Since the accuracy of a fresh sample on the "external" calibration curve was 92%, these results indicate that lipoic acid is stable in plasma for at least one week.

The stability of dihydrolipoic acid in plasma was also evaluated by spiking plasma at 0.5 mg/ml and storing it at -25° C. After approximately 20 hours, ca. 6% of the theoretical value was detected. In these samples a high amount of lipoic acid was present. Lipoic acid was also detected in the quality control samples of dihydrolipoic acid used for determination of the accuracy and precision. The quality control samples were processed immediately after spiking, indicating that dihydrolipoic acid is not stable in plasma. Because one of our goals was to detect potentially formed dihydrolipoic acid, sample pretreatment was optimized for the detection of dihydrolipoic acid. This means that the sample is immediately analyzed after blood sampling, and the pH is reduced to increase the stability of thiols. This has no effect on lipoic acid determination. However, one should keep in mind that by using this procedure an "external" calibration line, prepared in eluens instead of plasma, must be used.

The limit of detection of lipoic acid in plasma is 7.8 ng/ml at a signal to noise ratio of 3:1 taking into account a recovery of 92%. This limit of detection can be improved by decreasing the amount of ethanol/$H_3PO_4$ which is added to the plasma in the work-up procedure. However, for the pharmacokinetic study a limit of detection of 7.8 ng/ml was sufficient. The limit of detection of dihydrolipoic acid in plasma is 12.9 ng/ml at a signal to noise ratio of 3:1 taking into account a recovery of 70%.

The Pharmocokinetic Analysis

A male volunteer was given 1 gram R-lipoic acid. Thirty minutes after the administration, lipoic acid was detected in the plasma. Somewhat later, an unknown metabolite was observed which eluted at 5.5 min (peak nr. 6 in FIG. 2). Thereafter, a second unknown appeared which eluted at 4.7 min (peak nr. 5 in FIG. 2). Subsequently, ca. 45 after administration, bisnorlipoic acid could be detected (peak nr. 4 in FIG. 2). Neither dihydrolipoic acid nor tetranorlipoic acid were found. The time course of the plasma concentrations of lipoic acid, the two unknown metabolites and bisnorlipoic acid are shown in FIG. 3. Around 45 min a maximum in the lipoic acid concentration is reached. At 75 min a diet containing a high amount of fat was consumed. This coincided with an increase of the lipoic acid level (as seen as a second peak level of lipoic acid in FIG. 3). The time profile of the first unknown metabolite (peak nr. 6 in FIG. 2) parallels that of lipoic acid. The levels of the second unknown metabolite (peak nr. 5 in FIG. 2) and bisnorlipoic acid followed the same pattern as that of lipoic acid, although a short delay in the increase and decrease of these metabolites compared to lipoic acid was found (FIG. 3).

Elucidation of the Unknown Metabolite

In order to identify the unknown metabolites, the samples taken 69, 92 and 119 min were combined. The pooled sample was extracted and methylated as described in the materials and methods section. Applying the GC/MS method, pure lipoic acid methylester eluted at 10.46 min. The mass spectrum of lipoic acid methylester is depicted in FIG. 4. It shows the following characteristic peaks: m/z 220 ([M°]+), m/z 189 ([M—$CH_3O$]+), m/z 187 ([M—SH]+), m/z 161 ([M—$CH_3OCO$]+), m/z 155 ([M—SSH]+), m/z 123 ([155—$CH_3OH$]+), m/z 105 ([$C_3H_5S_2$]+, the 1,2-dithiolane ring structure). In the extract from plasma the peak detected at 10.47 min showed a mass spectrum which was identical to the spectrum obtained from the pure compound. Obviously, this peak results from lipoic acid present in the plasma.

The total ion current chromatogram was searched for metabolites of lipoic acid which are conceivable products of beta oxidation. The beta oxidation reaction sequence is depicted in the left-hand column of FIG. 5; the conceivable products which would result from a release from coenzyme A and subsequent methylation in our derivatization procedure are given in the right-hand column. The derivatized plasma sample was found to contain a compound with a molecular weight of 234 u, eluting at 12.20 min. This unknown metabolite was subsequently identified from its mass spectrum to be 3-ketolipoic acid (FIG. 5, IV). Assuming that the derivatized compound is the 3-ketolipoic acid methyl ester, the mass spectrum can be explained as follows: m/z 234 ([M°]+), m/z 219([M—$CH_3$]+), m/z 203 ([M—$CH_3O$]+), m/z 201 ([M—SH]+), m/z 169) ([M—SSH]+), m/z 119 ([$C_3H_5S_2CH_2$]+, the 1,2-dithiolane containing structure). Although the mass spectrum misses some features likely to be observed in the fragmentation of ionized 3-ketolipoic acid methyl ester, the identity of the compound can unequivocally be established. In analogy to lipoic acid methyl ester, the mass spectrum of the unknown metabolite contains fragments with an isotope pattern of two sulfur atoms (m/z 234, 219 and 203). In addition, the ionized compound loses 33 and 65 u ([M—SH]+, m/z 201 and [M—SSH]+, m/z 169) showing that the 1,2-dithiolane ring structure is present. Also the loss of 31 u ([M—$CH_3O$]+, m/z 203) and the presence of m/z 59 ([$OCOCH_3$]+) are indicative of the methyl ester moiety. The net mass excess of 14 u as compared to lipoic acid methyl ester must therefore be located between the ester and the 1,2-dithiolane moiety, implying the structure of an a, b or g keto-ester. The only abundant signals which provide a clue for the distinction of these three alternatives are found at m/z 73 and 74. The m/z 73 ions must have the structure [$CH_2C(O)OCH_3$]+, and would result from an inductive cleavage of the bond to the carbonyl carbon; this fragment rules out the a keto-ester option. The m/z 74 ions, most probably with the structure [$CH_2C(OH)OCH_3$]+, must result from a McLafferty rearrangement involving the methyl ester group, this requires the presence of a g H atom and effectively rules out the g keto-ester structure. Thus, the formation of ions m/z 73 and m/z 74 leads to the conclusion that the isomer has the b-keto ester structure. Note that other ions due to a carbonyl induced bond breaking, conceivably 133 ([$C_3H_5S_2CH_2CH_2$]+), and m/z 175 ([$C_3H_5S_2CH_2CH_2C(O)CH_2$]+) from a-cleavage and m/z 101 ([$C(O)CH_2C(O)OCH_3$]+) from inductive cleavage, at best have a low abundance; in addition the relatively abundant loss of 15 u (M—$CH_3$]+, m/z 219) and of 47 u could only result from quite specific fragmentation, e.g. some g keto-assisted methyl loss. In conclusion, numerous arguments support that the compound eluting at 12.20 min in the GC/MS experiments is 3-ketolipoic acid.

Several indications were found that the peak eluting at 5.5 min in HPLC (peak 6 in FIG. 2) is identical to 3-ketolipoic acid of which the methylester eluted in GC at 12.20 min. First, the physical properties of the compound eluting at peak 6 are as predicted for 3-ketolipoic acid. On the HPLC system the unknown metabolite shows less retention than lipoic acid, as expected for the more hydrophilic 3-ketolipoic acid. In the GC experiments, the methylester of the unknown metabolite eluted after the lipoic acid methylester which conforms to the expectation that 3-ketolipoic acid methylester is the less volatile of the two. Second, the unknown metabolite of lipoic acid must be oxidizable because, after HPLC separation, it is electrochemically detected. Indeed, 3-ketolipoic acid contains the 1,2-dithiolane ring structure which provides it with redox properties similar to those of lipoic acid. Up to this point, the compounds eluting in peak 5 and 6 both fulfill the physical and redox properties expected for 3-ketolipoic acid. However, as is shown in FIG. 3, the compound eluting in peak 6 reaches its maximum plasma level just before bisnorlipoic acid reaches its maximum. This indicates that, in the reaction sequence, the compound from peak 6 immediately precedes the formation of bisnorlipoic acid, as expected for 3-ketolipoic acid in the beta-oxidation sequence (FIG. 5). From this evidence it is inferred that the compound eluting at 0.5 min in HPLC is identical to that eluting at 12.20 min in GC/MS.

No signals originating from the conceivable methylated metabolites II and III (FIG. 5) could be detected, whereas the formation of bisnorlipoic acid could unequivocally be confirmed by GC/MS. Bisnorlipoic acid elutes at 8.6 min and shows typical signals in its mass spectrum: m/z 192 ([M°]+), m/z 161 ([M—$CH_3O$]+, m/z 127 ([M—SSH]+, m/z 118, m/z 105 ([$C_3H_5S_2$]+, the 1,2-dithiolane ring structure), and m/z 85. The identity was confirmed by HPLC/ECD and GC/MS analysis of the pure compound.

Synthesis of 3-keto-lipoic Acid

Figure 6:
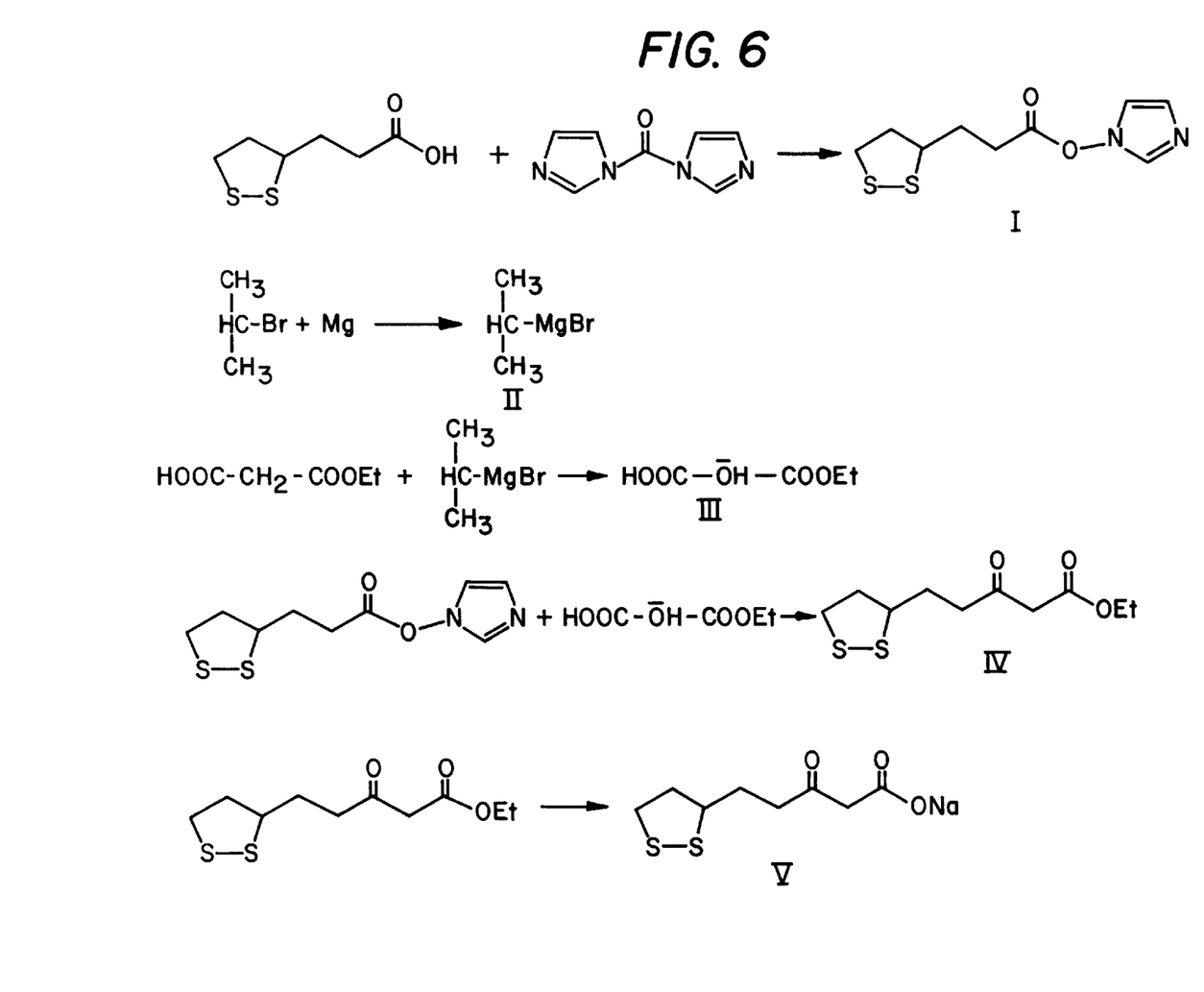
FIG. 6. The schematic diagram for synthesizing 3-keto lipoic acid from bisnor lipoic acid. The multistep reaction is carried out at room temperature and 0° C. during the formation of intermediates I, II, II IV. The final product V, 3-keto lipoic aicd, was precipitated from solution at 0° C., filtered and dried.

The compound 3-keto-lipoic acid can be synthesized according to the invention via the steps outlined in the schematic diagram of FIG. 6, and described herein below. The final 3-keto-lipoic acid product can be reduced to 3-hydroxy lipoic acid, 3-keto dihydrolipoic acid or 3-hydroxy dihydrolipoic acid in a manner known per se.

Synthesis of I

Bisnorlipoic acid (9.1 g) was dissolved in 50 ml THF (dry) and 7 g 1,1'-carbonyldiimidazol was added. The reaction mixture was stirred for 12 hours at room temperature.

Synthesis of II

To 50 ml THF (dry) was added: 2.73 g magnesium, 12.56 g 2-bromopropane and one crystal of iodine at room temperature. The reaction mixture was stirred until all the magnesium disappeared.

Synthesis of III

Potassium ethylmalonate (8.8 g) was dissolved in 10 ml water, and 1.1 equivalent of concentrated HCl (37%) was slowly (approximately 30 min) added. The solution was extracted 3 times with 150 ml diethyl ether. The combined diethyl ether layers were dried and evaporated at room temperature. The residue was dissolved in 25 ml THF and this solution was slowly added to the Grignard reagent at 0° C. After the addition, the reaction mixture was kept at room temperature and stirred for 2 hours.

Synthesis of IV

I was slowly added to III at 0° C. After the addition, the reaction mixture was kept at room temperature and stirred for 12 hours. To the reaction mixture, 250 ml trichloromethane was added, and this mixture was poured on 300 ml of ice. The pH of the water layer was adjusted to 4 using a 10% HCl solution. The trichloromethane layer was removed, and the water layer was extracted 3 times with 250 ml trichloromethane. The combined trichloromethane layers were washed 3 with a 10% solution of $NaHCO_3$. The trichloromethane layer was dried and the trichloromethane was evaporated at room temperature.

Synthesis of V

In 25 ml ethanol and 10 ml water, 1.1 equivalent of NaOH was dissolved. Slowly, a solution of IV in 10 ml ethanol was added. The mixture was refluxed for 1 hour. Ethanol was evaporated at room temperature. The water layer was adjusted to pH 2 using a 10% HCl solution, and extracted 3 times with 100 ml dichloroethane. The combined dichloroethane layers were washed once with 100 ml water, dried, and the dichloroethane was evaporated. To the residue, 1.05 equivalent of NaOH in ethanol (absolute) was added, and the mixture was cooled at 0° C. The resulting precipitate was filtered and dried.

Pharmaceutical Examples

The compounds according to the present invention can be administered in form of the free acids or their salts, esters or amides.

The amounts by weight, given in the patent, relate in each case to the free acids. When salts, esters or amides are used, the weights must be adapted correspondingly to the changed molecular weights.

The salts are synthesized by known methods (see also Patent EP-A 901213405). The pharmaceutical preparations generally contain 10 mg to 2 g of the compounds used pursuant to the invention as a single dose. After repeated administrations, the effective level attained in the body should be between 0.1 and 100 mg/kg of body weight.

The material is administered in the form of tablets, chewable tablets, sucking tablets, pills, capsules, granulates, coated tablets, effervescent tablets, effervescent powders, finished drink solutions, liquid forms for parenteral administration and aerosols. Finished drink solutions and liquid forms for parenteral administration can be alcoholic or aqueous solutions, suspensions and emulsions.

Preferred embodiments are, for example, tablets, which contain between 10 mg and 2 g of active substance, as well as solutions, which contain the active substance in amounts of between 1 mg and 200 mg per mL of liquid.

The doses can be administered, for example, 1 to 6 times daily or as an intravenous drip.

EMBODIMENTS

Example 1

Tablets with 100 mg of 3-keto Lipoic Acid 3-keto lipoic acid (250 g) is triturated uniformly with 750 g of microcrystalline cellulose. After the mixture is screened, 250 g of start (Starch 1500/Colorcon), 732.5 g of lactose, 15 g of magnesium stearate and 2.5 g of highly dispersed silica are admixed and the mixture is pressed into tablets weighing 800.0 mg. One tablet contains 100 mg of 3-keto lipoic acid. If necessary, the tablets can be coated in a conventional manner with a film, which is soluble or permeable to gastric juices.

Example 2

Ampules with 250 mg of 3-keto Lipoic Acid as Tromestamol Salt in 10 mL of Injection Solution 3-Keto lipoic acid (250 g), together with 352.3 g of trometamol (2-amino-2-(hydroxymethyl)-1,3-propylene glycol) is dissolved with stirring in a mixture of 9 liters of water for injection purposes and 200 g of 1.2-propylene glycol. The solution is made up to 10 liters with water for injection purposes and subsequently filtered through a glass fiber prefilter and then through a membrane filter with a pore size of 0.2 $\mu$m. The filtrate (10 mL amounts) is filled under aseptic conditions into 10 mL ampules. In 10 mL of injection solution, 1 ampule contains 250 mg of 3-keto lipoic acid as the trometamol salt.

Example 3

Ampules with 250 mg of 3-keto Lipoic Acid in 10 mL of Injection Solution

Trometamol (60 mg) and 1 g of the disodium salt of ethylenediaminetetraocetic acid are dissolved in 1.8 liters of water for injection purposes. Nitrogen is bubbled for 30 minutes through the solution. While the bubbling of nitrogen is continued, 2 g of sodium disulfite and subsequently 50 g of 3-keto lipoic acid are dissolved in the mixture. The solution is made up to a volume of 2 liters with water for injection purposes, through which nitrogen has been bubbled. After careful mixing, the solution is filtered through a membrane filter with a pore size of 0.2 $\mu$m and the filtrate is filled into 10 mL ampules under aseptic conditions, nitrogen being bubbled through the filtrate before and after it is filled into the ampules. One ampule contains 250 mg of 3-keto lipoic acid as the trometamol salt in 10 mL of solution.

What is claimed is:

1. A compound of the formula wherein X is H or both Xs represent a direct bond between the two sulfur atoms; $R_1$ is (=O) or —OH; and $R_2$ is H, Na, K or ($C_1$–$C_4$) alkyl.

2. The compound of claim 1 wherein $R_1$ is (=O); $R_2$ is H and both Xs together represent a direct bond between two sulfur atoms.

3. A method of reducing the symptoms associated with free radical mediated diseases comprising administering an effective amount of the compound of the formula wherein X is H or both Xs represent a direct bond between the two sulfur atoms; $R_1$ is (=O) or —OH; and $R_2$ is H, Na, K or ($C_1$–$C_4$) alkyl.

4. The method of claim 3 wherein $R_1$ is (=O); $R_2$ is H and both Xs together represent a direct bond between two sulfur atoms.

5. A method of treating free radical mediated diseases comprising administering an effective amount of the compound of the formula wherein X is H or both Xs together represent a direct bond between the two sulfur atoms; $R_1$ is (=O) or —OH; and $R_2$ is H, Na, K or ($C_1$–$C_4$)alkyl.

6. The method of claims 3 or 5 wherein the free radical mediated disease is diabetic polyneuropathy, liver cirrhosis or metal intoxication.

* * * * *